(12) United States Patent
Buckton et al.

(10) Patent No.: US 9,366,754 B2
(45) Date of Patent: Jun. 14, 2016

(54) ULTRASOUND IMAGING SYSTEM AND METHOD

(75) Inventors: Daniel John Buckton, Zipf (AT); Christian Fritz Perrey, Zipf (AT); Dieter Claus Hoenigmann, Wiener Neustadt (AT); Armin Schoisswohl, Wels (AT)

(73) Assignees: General Electric Company, Schnectady; n22e.u., Weiner Neustadt (AU); myotise.u., Wels (AU)

( * ) Notice: Subject to any disclaimer, the term of this patent is extended or adjusted under 35 U.S.C. 154(b) by 82 days.

(21) Appl. No.: 13/588,105

(22) Filed: Aug. 17, 2012

(65) Prior Publication Data

US 2014/0052000 A1 Feb. 20, 2014

(51) Int. Cl.
| | | |
|---|---|---|
| *A61B 8/13* | (2006.01) | |
| *A61B 8/08* | (2006.01) | |
| *G01S 7/52* | (2006.01) | |
| *A61B 8/14* | (2006.01) | |
| *A61B 8/00* | (2006.01) | |
| *G01S 15/89* | (2006.01) | |
| *A61B 5/0444* | (2006.01) | |

(52) U.S. Cl.
CPC ............ *G01S 7/52087* (2013.01); *A61B 8/0866* (2013.01); *A61B 8/0883* (2013.01); *A61B 8/145* (2013.01); *A61B 8/466* (2013.01); *A61B 8/469* (2013.01); *A61B 8/483* (2013.01); *A61B 8/486* (2013.01); *A61B 8/5246* (2013.01); *A61B 8/5253* (2013.01); *A61B 8/5284* (2013.01); *G01S 7/52063* (2013.01); *G01S 7/52065* (2013.01); *G01S 15/8925* (2013.01); *G01S 15/8993* (2013.01); *A61B 8/485* (2013.01); *A61B 8/488* (2013.01); *A61B 8/543* (2013.01)

(58) Field of Classification Search
CPC ............ G01S 7/52087; G01S 7/52063; G01S 7/52065; G01S 15/8993; G01S 15/8925; A61B 8/5246; A61B 8/5253; A61B 8/5284; A61B 8/0866; A61B 8/0883; A61B 8/145; A61B 8/466; A61B 8/469; A61B 8/483; A61B 8/485; A61B 8/486; A61B 8/488; A61B 8/543

See application file for complete search history.

(56) References Cited

U.S. PATENT DOCUMENTS

| | | | | |
|---|---|---|---|---|
| 6,889,071 | B2 * | 5/2005 | Saranathan et al. | 600/413 |
| 8,233,687 | B2 * | 7/2012 | Kurita | A61B 8/08 382/128 |
| 2008/0183092 | A1 * | 7/2008 | Smith et al. | 600/511 |
| 2008/0287790 | A1 * | 11/2008 | Li | 600/437 |

(Continued)

OTHER PUBLICATIONS

Ali et al., "Signal Processing Overview of Ultrasound Systems for Medical Imaging". White Paper, Texas Instruments, 2008.*

(Continued)

*Primary Examiner* — Long V Le
*Assistant Examiner* — Colin T Sakamoto (57) ABSTRACT

An ultrasound imaging system and method includes acquiring first 4D ultrasound data of a first partial volume for a first period of time that is longer than an estimated cardiac period and acquiring second 4D ultrasound data of a second partial volume for a second period of time that is longer than the estimated cardiac period. The system and method includes combining the first 4D ultrasound data with the second 4D ultrasound data to generate 4D ultrasound data of a region-of-interest. The system and method also includes generating and displaying an image based on the 4D ultrasound data.

18 Claims, 4 Drawing Sheets

(56) References Cited

U.S. PATENT DOCUMENTS

2009/0198134 A1* 8/2009 Hashimoto et al. ........... 600/443
2010/0168573 A1 7/2010 Sherrill
2011/0201935 A1 8/2011 Collet-Billon et al.
2012/0123267 A1 5/2012 Dow et al.

OTHER PUBLICATIONS

Brattain et al., "Real-Time 4D Ultrasound and Visualization" Medical Image Computing and Computer-Assisted Intervention—MICCAI 2011 vol. 6891 of the series Lecture Notes in Computer Science pp. 105-112, 14th International Conference, Toronto, Canada, Sep. 18-22, 2011, Proceedings, Part I.*

Liebling et al., "Nonuniform Temporal Alignment of Slice Sequences for Four-Dimensional Imaging of Cyclically Deforming Embryonic Structures", 3rd IEEE International Symposium on Biomedical Imaging: Nano to Macro, 2006.*

* cited by examiner

ULTRASOUND IMAGING SYSTEM AND METHOD

FIELD OF THE INVENTION

This disclosure relates generally to an ultrasound imaging system and a method for generating 4D ultrasound data of a region-of-interest by acquiring 4D ultrasound data for a plurality of partial volumes.

BACKGROUND OF THE INVENTION 2D array probes coupled with current generation ultrasound systems are not fast enough to acquire clinically suitable volume sizes for applications such as fetal heart imaging. It is currently not possible to achieve both the required temporal resolution and the required spatial resolution from a single volume acquired with a conventional 2D array probe.

As a result, some conventional ultrasound systems slowly sweep across an entire volume, acquiring a 2D image frames at distinct locations during the sweep. For example, the sweep may take 8-12 seconds for a typical fetal heart. During the time of the sweep, the fetal heart may beat approximately 16 to 30 times. Phase data indicating the cardiac phase at the acquisition of each 2D image frame may be acquired based on data from M-mode acquisitions. According to conventional techniques such as STIC (Spatio-temporal image correlation), images of the entire volume at various cardiac phases are "synthesized" using frames from discrete cardiac cycles. In other words, each volume is not acquired during the same cardiac cycle. Instead, each slice or image of the volume is acquired during a different cardiac cycle. Then, the "synthesized" volumes for each of the cardiac phases may be placed in a sequence representing a complete cardiac cycle. A user may then select to view an image of any plane from within the volume or the user may view a rendering of some or all of the volume.

Conventional techniques like STIC suffer from at least two problems: it takes too long to acquire all of the data; and the resulting volume has limited resolution in a elevation direction. Specifically, since only one 2D image frame is selected from each cardiac cycle, the resolution in the elevation direction is limited to the number of cardiac cycles of the acquisition. Using a technique that requires a long acquisition time also increases the likelihood of acquiring data with motion artifacts. For example, both the clinician holding the 2D array probe and the patient are more likely to move during a longer acquisition. Any relative movement between the 2D array probe and the patient's anatomy being scanned may introduce motion artifacts. Also, any irregularities in a patient's heart movements may result in additional motion or spatial artifacts.

For these and other reasons an improved method and ultrasound imaging system for acquiring 4D ultrasound data is desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes dividing a region-of-interest into a plurality of partial volumes including a first partial volume and a second partial volume. The method includes acquiring first 4D ultrasound data of the first partial volume during a first period of time that is longer than an estimated cardiac period. The method includes acquiring second 4D ultrasound data of the second partial volume during a second period of time that is longer than the estimated cardiac period, wherein the second period of time occurs after the first period of time. The method includes combining the first 4D ultrasound data with the second 4D ultrasound data to generate 4D ultrasound data of the region-of-interest. The method includes generating an image based on the 4D ultrasound data of the region-of-interest and displaying the image.

In an embodiment, a method of ultrasound imaging includes determining an estimated cardiac period, dividing a region-of-interest into a plurality of partial volumes including a first partial volume and a second partial volume. The method includes acquiring first 4D ultrasound data of the first partial volume over a first period of time that is longer than the estimated cardiac period. The method includes acquiring first phase data during the process of acquiring the first 4D ultrasound data and associating the first phase data with the first 4D ultrasound data. The method includes acquiring second 4D ultrasound data of the second partial volume over a second period of time that is longer than the estimated cardiac period. The second period of time occurs after the first period of time. The method includes acquiring second phase data during the process of acquiring the second 4D ultrasound data and associating the second phase data with the second 4D ultrasound data. The method includes interpolating the first 4D ultrasound data to generate first interpolated 4D ultrasound data, interpolating the second 4D ultrasound data to generate second interpolated 4D ultrasound data, and combining the first interpolated 4D ultrasound data with the second interpolated 4D ultrasound data to generate 4D ultrasound data of the region-of-interest over a complete cardiac cycle. The method includes generating an image based on the 4D ultrasound data of the region-of-interest, and displaying the image.

In another embodiment, an ultrasound imaging system includes a probe, a display device, and a processor in electronic communication with the probe and the display device. The processor is configured to divide a region-of-interest into a first partial volume and a second partial volume. The processor is configured to determine an estimated cardiac period. The processor is configured to control the probe to acquire first 4D ultrasound data of the first partial volume for a first period of time that is longer than the estimated cardiac period and to control the probe to acquire second 4D ultrasound data of the second partial volume for a second period of time that is longer than the estimated cardiac period. The processor is configured to associate phase data with both the first 4D ultrasound data and the second 4D ultrasound data and to combine the first 4D ultrasound data with the second 4D ultrasound data based on the phase data to generate 4D ultrasound data of the region-of-interest. The processor is also configured to generate an image based on the 4D ultrasound data of the region-of-interest and to display the image on the display device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
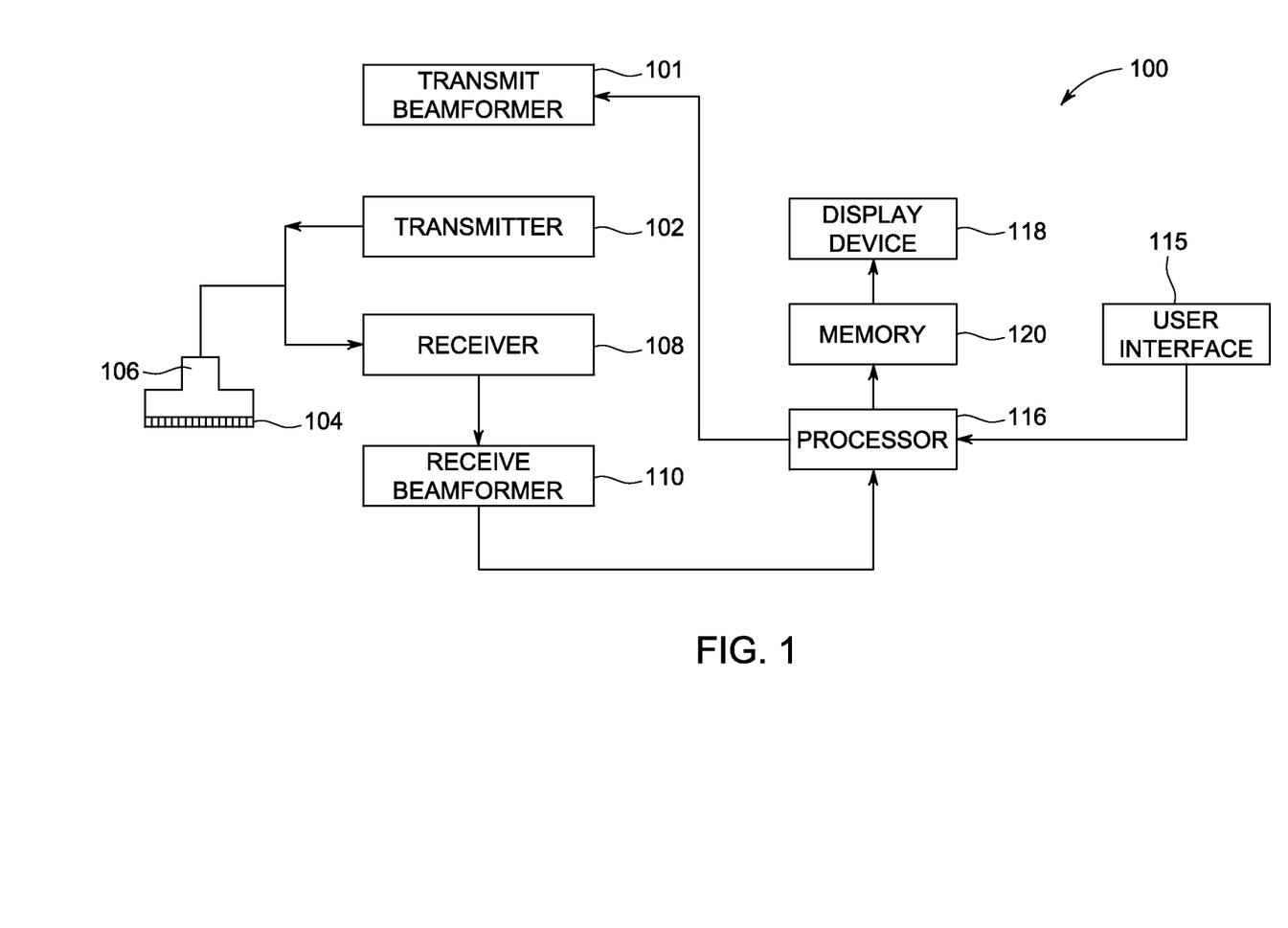
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). The probe 106 may be an 2D array probe according to an embodiment. However, any other type of probe that is fully steerable in an elevation direction and capable of acquiring four-dimensional (4D) ultrasound data may be used according to other embodiments. For purposes of this disclosure, the term four-dimensional ultrasound data, or 4D ultrasound data, is defined to include ultrasound data including multiple volumes of a region-of-interest acquired over a period of time. The 4D ultrasound data contains information about how a volume changes over time. Each of the volumes may include a plurality of 2D images or slices. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like.

The ultrasound imaging system 100 also includes a processor 116 to control the transmit beamformer 101, the transmitter 102, the receiver 108 and the receive beamformer 110. The processor 116 is in electronic communication with the probe 106. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire and display data a real-time volume-rate of 7-20 volumes/sec. However, it should be understood that the real-time frame rate may be dependent on the length of time that it takes to acquire each volume of data. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar volume-rate. Other embodiments may acquire and display data at different rates. For example, some embodiments may acquire data at a volume-rate of less than 10 Hz or greater than 30 Hz depending on the size of the volume and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
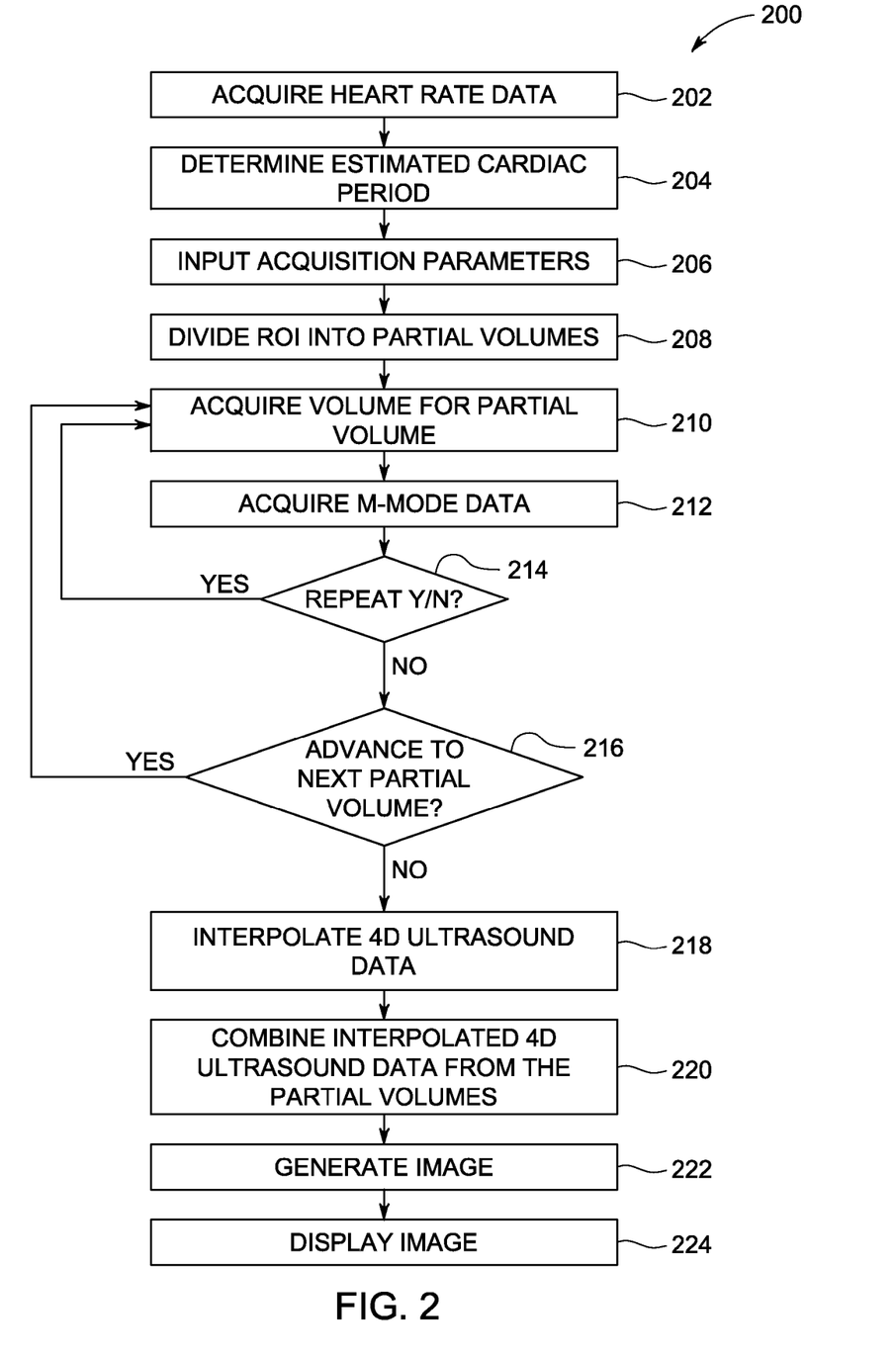
FIG. 2 is a flow chart of a method in accordance with an embodiment.

FIG. 2 is a flow chart of a method in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the display of an image generated from 4D ultrasound data acquired as a plurality of partial volumes. The method 200 will be described according to an exemplary embodiment where the method 200 is implemented by the processor 116 of the ultrasound imaging system 100 of FIG. 1. Additionally, the method 200 will be described according to an embodiment where 4D ultrasound data of a fetal heart is acquired. It should be appreciated that according to other embodiments, the method 200 may be used to acquire 4D ultrasound data of some or all of an adult heart as well.

Referring to FIGS. 1 and 2, at step 202 heart rate data is acquired. According to an embodiment concerning a fetal heart, acquiring heart rate data may include acquiring ultrasound data and analyzing the resulting ultrasound data to identify the heart rate or an estimated heart rate. For example, images may be acquired over a period of time and image processed to determine an average heart rate. Or, M-mode data may be acquired along one or more lines and analyzed to determine the heart rate. According to yet other embodiments, a ECG or fetal ECG may be used to acquire phase data or to determine one or more triggers per cardiac cycle. The triggers may be associated with a particular phase of the cardiac cycle and, as such, the triggers may be used to determine an approximation of the patient's heart rate.

At step 204, an estimated cardiac period is determined based on the heart rate data. According to an embodiment, the processor 116 may be used to calculate the estimated cardiac period. The estimated cardiac period may be determined from one or more cardiac cycles worth of heart rate data. The estimated cardiac period may be determined with other techniques according to additional embodiments.

Next, at step 206, a user may enter desired acquisition parameters through the user interface 115. The acquisition parameter may include parameters such as the selection of a region-of-interest, or ROI, resolution, depth, image mode, desired temporal resolution, and the like. For purposes of this disclosure, the term ROI is defined to include a volume. Some or all of the acquisition parameters may be preselected as part of a default setting on the ultrasound imaging system 100.

At step 208, the processor 116 divides the ROI into a plurality of partial volumes. The processor 116 may determine the size and/or the distribution of the partial volumes based on the acquisition parameters that were inputted at step 206 and the technical capabilities of the ultrasound imaging system 100, including specifically the 2D array probe 106. According to other embodiments, the user may manually select the positions and/or the geometry of the partial volumes.

Figure 3:
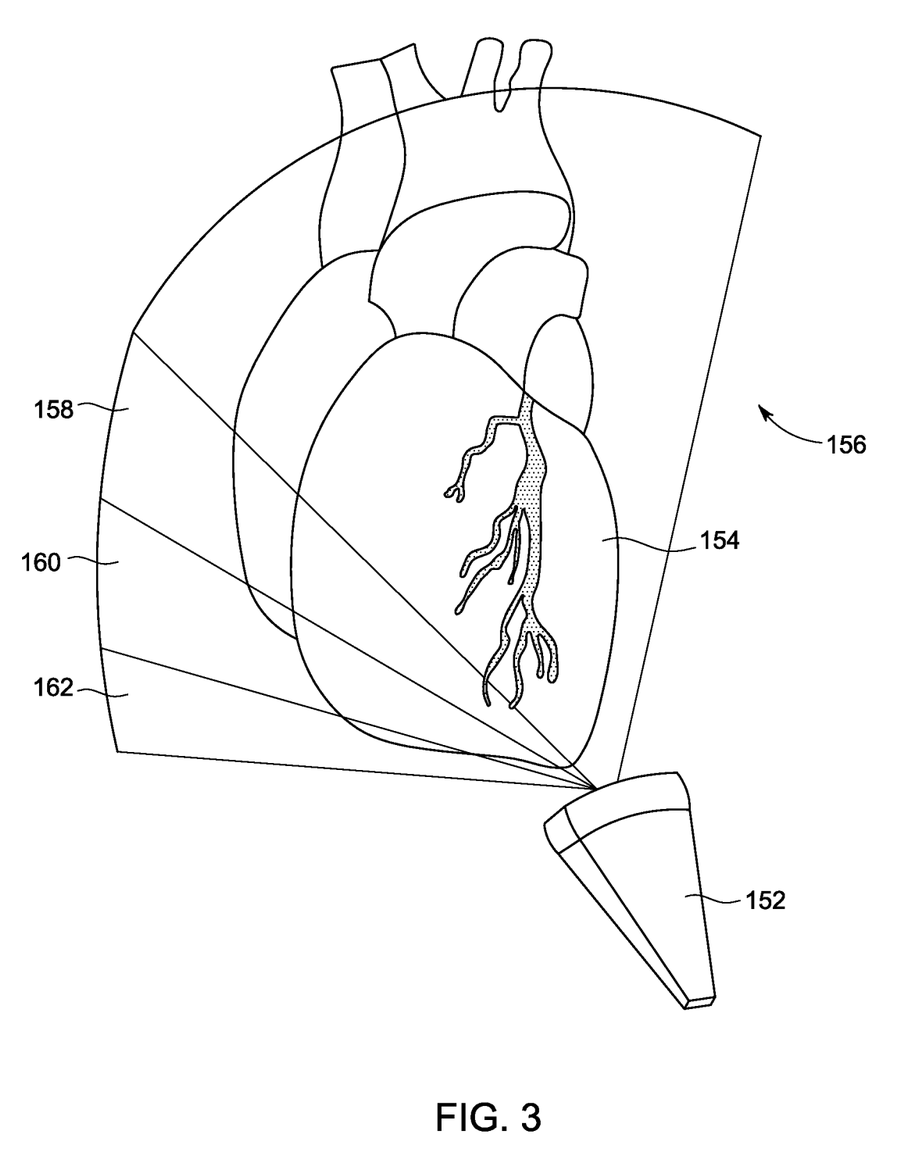
FIG. 3 is a schematic representation of a probe and a region-of-interest divided into three partial volumes in accordance with an embodiment.

FIG. 3 is a schematic representation of an ROI 156 divided into three partial volumes in accordance with an embodiment. FIG. 3 also includes a 2D array probe 152 and a fetal heart 154. The ROI 156 is divided into a first partial volume 158, a second partial volume 160, and a third partial volume 162. When combined, the first partial volume 158, the second partial volume 160, and the third partial volume 162 cover the entire ROI 156. According to the embodiment shown in FIG. 3, the partial volumes 158, 160, 162 do not overlap. However, according to other embodiments, each of the partial volumes 158, 160, 162 may overlap with any adjacent partial volumes. That is, the first partial volume 158 may overlap with the second partial volume 160; the second partial volume 160 may overlap with both the first partial volume 158 and the third partial volume 162; and the third partial volume 162 may overlap with the second partial volume 160. It should be appreciated that the ROI 156 may be divided into a different number of partial volumes according to other embodiments. The method 200 may be used to acquire data for any number of partial volumes greater than or equal to 2.

Referring to FIGS. 1, 2, and 3, at step 210, the processor 116 acquires a volume of data for the first partial volume 158. The processor 116 controls the transmit beamformer 101, the transmitter 102, the probe 106, the receive 108, and the receive beamformer 110 to control the acquisition of the ultrasound data. According to an embodiment, the processor 116 may acquire ultrasound data of the first partial volume 158 through the acquisition of a plurality of 2D image frames at different elevational angles within the first partial volume 158. Acquiring data of a volume by acquiring a plurality of 2D image frames is well-known by those skilled in the art. Next at step 212, the processor controls the acquisition of M-mode data. Acquiring M-mode data includes acquiring data along a scan line at different points in time. M-mode data is very fast to acquire and is typically used for determining motion. The acquisition of the M-mode data may be interleaved with the acquisition of 4D ultrasound data in other embodiments.

At step 214, the processor 116 determines if it is desired to acquire another volume of ultrasound data of the first partial volume 158. If it is desired to acquire an additional volume of ultrasound data, the method 200 returns to step 210, and steps 210 and 212 are repeated. The speed of acquiring each volume of the first partial volume 158, or any of the other partial volumes, may vary depending upon the acquisition parameters selected at step 206 and the specifications of the ultrasound imaging system 100. However, it should be possible to acquire many volumes of a particular partial volume during a single cardiac cycle. According to an embodiment, the processor 116 will control the rest of the ultrasound imaging system 100 so that 4D ultrasound data is acquired of the first partial volume 158 for an amount of time longer than the estimated cardiac period calculated during step 204. In other words, the method 200 repeats steps 210, 212, and 214 for a predetermined amount of time in order to acquire a plurality of volumes over time, which will be referred to as 4D ultrasound data. According to another embodiment, the processor 116 may use triggers from an ECG or fetal ECG to insure that the 4D ultrasound data has been acquired for a period of time longer than the patient's cardiac period instead of or in addition to determining an estimated cardiac period. After acquiring 4D ultrasound data of the first partial volume for a period of time longer than the estimated cardiac period. At step 214, the processor 116 determines that it is not desired to acquire additional volumes of the first partial volume 158 and the method 200 advances to step 216.

At step 216, the processor 116 determines if it is desired to advance to the next partial volume. According to an exemplary embodiment, after acquiring a first plurality of volumes of the first partial volume 158, it is desired to advance to the next, or second partial volume 160. The method 200 then repeats steps 210, 212, and 214 until a second plurality of volumes have been acquired of the second partial volume 160. The second plurality of volumes show the second partial volume 160 over time and collectively may be referred to as the second 4D ultrasound data. The processor 116 controls the acquisition so that volumes of the second partial volume 160 are repeatedly acquired for a period of time that is greater than the estimated cardiac period determined during step 204. After repeating steps 210, 212, and 214 for the desired amount of time and acquiring the second 4D ultrasound data, the processor 116 determines that it is not desired to acquire another volume of the second partial volume 160 at step 214 and the method 200 advances to step 216.

At step 216, the processor 116 determines that it is desired to advance to the next partial volume, which may be the third partial volume 162 according to an exemplary embodiment. The method 200 repeats steps 210, 212, and 214 in order to acquire third 4D ultrasound data. According to an exemplary embodiment, the third 4D ultrasound data shows how the third partial volume 162 changes over time. As with the first partial volume 158 and the second partial volume 160, the processor 116 may control the rest of the ultrasound imaging system 100 to acquire 4D ultrasound data of the third partial volume 162 for a period of time longer than the estimated cardiac period.

The processor 116 may divide the phase data acquired at step 212 during multiple iterations of the method 200 into first phase data acquired during the process of acquiring the first 4D ultrasound data, second phase data acquired during the process of acquiring the second 4D ultrasound data, and third phase data acquired during the process of acquiring the third 4D ultrasound data. According to other embodiments, the phase data may be determined during post-processing of the 4D ultrasound data through image processing techniques. The processor 116 may then associate the phase data with the individual volumes that were acquired as part of the 4D ultrasound data. For example, the processor 116 may associate each volume that is part of the 4D ultrasound data for each of the partial volumes with a particular phase.

After acquiring 4D ultrasound data for each of the three partial volumes 158, 160, and 162, at step 216 the processor 116 determines that enough 4D ultrasound data has been acquired and that it is not desired to advance to the next partial volume. Therefore, the method 200 advances to step 218.

Figure 4:
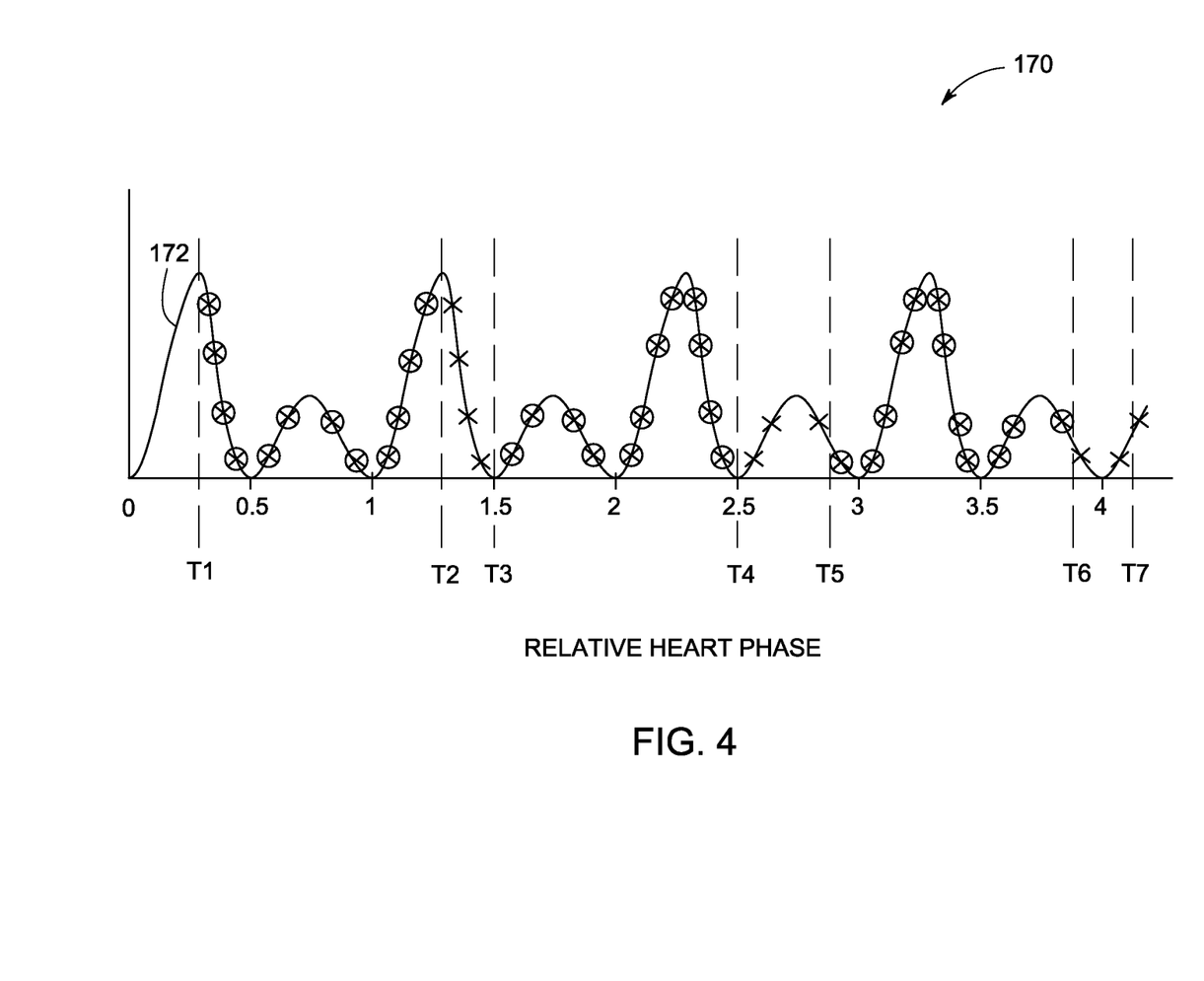
FIG. 4 is a graph showing the timing of volume acquisitions with respect to relative heart phase in accordance with an embodiment.

FIG. 4 is a graph showing the timing of volume acquisitions with respect to relative heart phase. The graph 170 depicts slightly more than 4 cardiac cycles. The graph 170 will be described according to an exemplary embodiment where the data were collected according to the method 200 (shown in FIG. 2). The numbers along the x-axis (0, 0.5, 1, 1.5, 2, 2.5, 3, 3.5, and 4) show the relative heart phase. For illustrative purposes, a trace 172 is shown. The trace 172 has a shape similar to that of an ECG trace to more clearly illustrate the relative heart phase. The trace 172 is marked with an "X" at each time where a volume of data is acquired.

Referring now to both FIG. 2 and FIG. 4, each "X" on the trace 172 represents the time that a volume was acquired at step 210 of the method 200. Each "X" represents the acquisition of a volume of one of the partial volumes 158, 160, or 162. According to an embodiment, the 4D ultrasound acquisition for the first partial volume 158 (shown in FIG. 3) begins at time T1. The cardiac period is from time T1 to time T2. The processor 116 controls the acquisition of 4D ultrasound data of the first partial volume 158 for a period of time longer than the estimated cardiac period determined at step 204. Referring the FIG. 4, the acquisition of 4D ultrasound data for the first partial volume 158 extends all the way until time T3, which is longer than the cardiac period.

Starting at time T3, the method 200 acquires 4D ultrasound data for the second partial volume 160. The cardiac period lasts from time T3 until time T4. However, the acquisition of 4D ultrasound data of the second partial volume 160 extends all the way until time T5, which is also longer than the cardiac period and the estimated cardiac period. Likewise, the method 200 acquires 4D ultrasound data for the third partial volume 162 starting at time T5. The cardiac period is from time T5 until time T6, but the acquisition of 4D ultrasound data of the third partial volume 162 extends until time T7, which is a period of time longer than both the cardiac period and the estimated cardiac period.

After 4D ultrasound data has been acquired for each of the three partial volumes, the method 200 advances to step 218. At step 218, the processor 116 interpolates the 4D ultrasound data. The 4D ultrasound data may include first 4D ultrasound data of the first partial volume 158, second 4D ultrasound data of the second partial volume 160, and third 4D ultrasound data of the third partial volume 162. According to an embodiment, only the volumes represented by an "X" surrounded by a circle may be used during the interpolation process of step 218. The interpolation results in the creation of first interpolated 4D ultrasound data for the first partial volume 158, second interpolated 4D ultrasound data for the second partial volume 160, and third interpolated 4D ultrasound data for the third partial volume 162. Since the 4D ultrasound data for each of the partial volumes includes a sequence of volumes, for high quality 4D images of the whole ROI, it is necessary to combine volumes with the same phase. Since the 4D ultrasound acquisitions are not gated to the cardiac cycle during acquisition, the relative phases of the volumes is not known. Therefore once phase data has been associated with the 4D ultrasound data, it may be necessary to interpolate between some or all of the volumes in order to generate temporally synchronous volumes from each of the partial volumes. For example, the processor 116 may determine first how many volumes are needed to cover the cardiac cycle and then the processor 116 may calculate the desired phase for each of the volumes. Using the desired phase information, the processor 116 then determines which acquired volumes to use as the basis for each interpolation. Many different types of interpolation algorithms may be used including linear, step-wise linear, nearest neighbor, and cubic.

After the interpolation has been completed at step 218, the method 200 advances to step 220 where the 4D ultrasound data of the partial volumes are combined. As described previously, the interpolation at step 218 insures each of the 4D interpolated ultrasound datasets includes volumes at the same relative phases. Since all the volumes are at the same relative phases, it is possible to spatially stitch together the volumes from each of the interpolated 4D ultrasound datasets representing the individual partial volumes. That is, volumes representing each of the three partial volumes may be combined at a plurality of different cardiac phases. During step 220, 4D ultrasound data of the ROI has been generated that is representative of a complete cardiac cycle based on the 4D interpolated ultrasound data for each of the partial volumes.

Next, at step 222, the processor 116 generates an image from the 4D ultrasound data. The image be a static image of a plane, a volume-rendered image, a cine image of a plane, or any other type of image generated from the 4D ultrasound data. According to an embodiment, the user may manually select the location of the plane based on inputs from the user interface 115, or the processor 116 may automatically select one or more standard planes. At step 224, the image is displayed on the display device 118.

It is known by those skilled in the art that the fetal heart rate may vary considerably during the process of acquiring ultrasound data. For example, it is quite common for the fetal heart rate to vary as much as 10-15% within only a few heartbeats. By ensuring that the 4D ultrasound data of each partial volume is acquired for a period of time that is longer than the estimated cardiac period, the method 200 increases the likelihood of acquiring enough 4D ultrasound data for each of the partial volumes to include all the required phases of the cardiac cycle, even if the patient's heart rate were to vary by 15% or more. For example, by acquiring 4D ultrasound data of a partial volume for at least 15% longer than an estimated cardiac period, the method insures the acquisition of volumes representing a whole cardiac cycle, even if the patient's heart rate were to increase by 15%. Therefore, by acquiring 4D ultrasound data for a period of time that is longer than the estimated cardiac period, the method 200 is robust enough to easily accommodate fluctuations in heart rate without requiring the acquisition of additional ultrasound data. As discussed above, according to an exemplary embodiment, it may be desirable to have the 4D ultrasound data acquired for a period of time approximately 15% longer than the estimated cardiac period. This should capture enough 4D ultrasound data to manage the most commonly occurring heart rate fluctuations. According to another embodiment, it may be desirable to acquire 4D ultrasound data for each of the partial volumes for a period of time approximately 30% longer than the estimated cardiac period. This would provide an additional buffer against fluctuating heart rates and still result in a much shorter overall acquisition time compared with conventional techniques. According to other embodiments, it may desirable to acquire 4D ultrasound data for a period of time that is at least 100% longer than the estimated cardiac period. By acquiring 4D ultrasound data for a period of time that is 2 times as long as the estimated cardiac period, the processor 116 would have additional volumes to choose from during the interpolation phase. For example, only a limited subset of the 4D ultrasound data acquired over 2 or more cardiac cycles for each partial volume may be selected based on quality criteria in order to generate a dataset with improved quality. For example, the 4D ultrasound data may be examined for motion artifacts, contrast, image stability, edge detection or any other criterion potentially related to quality. According to other embodiments, the 4D ultrasound data for each partial volume may be acquired for a period of time that is within a range of 115% to 230% of the estimated cardiac period. The range of 115% to 230% of the estimated cardiac period allows for the collection of two complete cardiac cycles of 4D ultrasound data for each of the partial volumes, even if the heart rate were to increase 15% during the acquisition of the 4D ultrasound data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
dividing a region-of-interest into a plurality of partial volumes including a first partial volume and a second partial volume, wherein the first partial volume is different from the second partial volume;
acquiring first 4D ultrasound data exclusively from the first partial volume with a probe during a first period of time that is longer than an estimated cardiac period, wherein acquiring the first 4D ultrasound data comprises making multiple sweeps of the complete first partial volume in order to acquire a first sequence of volumes of the entire first partial volume, where each of the multiple sweeps is of the entire first partial volume, wherein each volume in the first sequence of volumes is acquired by acquiring a first plurality of 2D image frames from the first partial volume and each of the first plurality of 2D image frames is acquired from a distinct position within the first partial volume, where ultrasound data is acquired from only the first partial volume, and not from any other of the plurality of partial volumes, during the first period of time;
acquiring second 4D ultrasound data exclusively from the second partial volume with the probe during a second period of time that is longer than the estimated cardiac period, wherein the second period of time occurs after the first period of time, wherein acquiring the second 4D ultrasound data comprises making multiple sweeps of the complete second partial volume in order to acquire a second sequence of volumes of the entire second partial volume, where each of the multiple sweeps is of the entire second partial volume, wherein each volume in the second sequence of volumes is acquired by acquiring a second plurality of 2D image frames from the second partial volume and each of the second plurality of 2D image frames is acquired from a distinct position within the second partial volume, where ultrasound data is acquired only from the second partial volume, and not from any other of the plurality of partial volumes, during the second period of time, and where the probe is in a single stationary position during both the acquisition of the first 4D ultrasound data and the second 4D ultrasound data;
combining with a processor the first 4D ultrasound data acquired from the first partial volume with the second 4D ultrasound data acquired from the second partial volume to generate 4D ultrasound data of the region-of-interest;
generating an image based on the 4D ultrasound data of the region-of-interest; and
displaying the image on a display device.

2. The method of claim 1, further comprising estimating a heart rate before acquiring the first 4D ultrasound data and the second 4D ultrasound data and using the heart rate to determine the estimated cardiac period.

3. The method of claim 1, further comprising acquiring phase data during the process of acquiring the first 4D ultrasound data and second 4D ultrasound data.

4. The method of claim 3, further comprising associating phase data with both the first 4D ultrasound data and the second 4D ultrasound data, and wherein said combining the first 4D ultrasound data with the second 4D ultrasound comprises combining the first 4D ultrasound data with the second 4D ultrasound data based on the phase data.

5. The method of claim 3, wherein said acquiring the phase data comprises acquiring M-mode data during the process of acquiring the first 4D ultrasound data and the second 4D ultrasound data.

6. The method of claim 3, wherein said acquiring the phase data comprises acquiring the phase data with a fetal ECG.

7. The method of claim 1, wherein the first period of time is at least 15% longer than the estimated cardiac period.

8. The method of claim 1, wherein the first period of time is at least 30% longer than the estimated cardiac period.

9. The method of claim 1, wherein the first period of time is at least 100% longer than the estimated cardiac period.

10. The method of claim 1, further comprising interpolating with the processor the first 4D ultrasound data to generate first interpolated 4D ultrasound data before combining the first 4D ultrasound data with the second 4D ultrasound data.

11. The method of claim 10, further comprising the step of interpolating with the processor the second 4D ultrasound data to generate second interpolated 4D ultrasound data before combining the first 4D ultrasound data with the second 4D ultrasound data.

12. An ultrasound imaging system comprising:
a probe;
a display device; and
a processor in electronic communication with the probe and the display device, wherein the processor is configured to:
divide a region-of-interest into a plurality of partial volumes including a first partial volume and a second partial volume wherein the first partial volume is different from the second partial volume;
control the probe to acquire first 4D ultrasound data exclusively from the first partial volume during a first period of time that is longer than an estimated cardiac period, wherein acquiring the first 4D ultrasound data comprises making multiple sweeps of the complete first partial volume in order to acquire a first sequence of volumes of the entire first partial volume, where each of the multiple sweeps is of the entire first partial volume, wherein each volume in the first sequence of volumes is acquired by acquiring a first plurality of 2D image frames from the first partial volume and each of the first plurality of 2D image frames is acquired from a distinct position within the first partial volume, and where the processor is configured to acquire ultrasound data from only the first partial volume, and not from any other of the plurality of partial volumes during the first period of time;
control the probe to acquire second 4D ultrasound data exclusively from the second partial volume during a second period of time that is longer than the estimated cardiac period, wherein the second period of time occurs after the first period of time, wherein acquiring the second 4D ultrasound data comprises making multiple sweeps of the complete second partial volume in order to acquire a second sequence of volumes of the entire-second partial volume, where each of the multiple sweeps is of the entire second partial volume, wherein each volume in the second sequence of volumes is acquired by acquiring a second plurality of 2D image frames from the second partial volume and each of the second plurality of 2D image frames is acquired from a distinct position within the second partial volume, where the processor is configured to acquire ultrasound data from only the second partial volume, and not from any other of the plurality of partial volumes, during the second period of time, and where the probe is in a single stationary position during both the acquisition of the first 4D ultrasound data and the second 4D ultrasound data;
combine the first 4D ultrasound data acquired from the first partial volume with the second 4D ultrasound data acquired from the second partial volume to generate 4D ultrasound data of the region-of-interest;
generate an image based on the 4D ultrasound data of the region-of-interest; and
display the image on the display device.

13. The ultrasound imaging system of claim 12, wherein the processor is further configured to acquire phase data during the process of acquiring the first 4D ultrasound data and the second 4D ultrasound data.

14. The ultrasound imaging system of claim 13, wherein the processor is configured to acquire phase data by acquiring M-mode data during the process of acquiring the first 4D ultrasound data and the second 4D ultrasound data.

15. The ultrasound imaging system of claim 12, wherein the first period of time is at least 15% longer than the estimated cardiac period.

16. The ultrasound imaging system of claim 12, wherein the first period of time is at least 30% longer than the estimated cardiac period.

17. The ultrasound imaging system of claim 12, wherein the processor is further configured to interpolate the first 4D ultrasound data to generate first interpolated 4D ultrasound data before combining the first 4D ultrasound data with the second 4D ultrasound data.

18. The ultrasound imaging system of claim 17, wherein the processor is further configured to interpolate the second 4D ultrasound data to generate second interpolated 4D ultrasound data before combining the first 4D ultrasound data with the second 4D ultrasound data.

* * * * *